United States Patent [19]

Winquist

[11] Patent Number: 5,766,180
[45] Date of Patent: Jun. 16, 1998

[54] NAIL EXTRACTION KIT AND METHOD

[76] Inventor: Robert A. Winquist, 2311 Fifth Ave. North, Seattle, Wash. 98109

[21] Appl. No.: 509,329

[22] Filed: Jul. 31, 1995

[51] Int. Cl.$^6$ ................................... A61B 17/58
[52] U.S. Cl. ........................ 606/104; 606/62; 606/67
[58] Field of Search ........................ 606/104, 62, 63, 606/95, 72, 99, 100, 59, 67; 604/170, 264, 164, 93

[56] References Cited

U.S. PATENT DOCUMENTS

| | | | |
|---|---|---|---|
| D. 290,399 | 6/1987 | Kitchens | D24/26 |
| 3,208,450 | 9/1965 | Abelson | 128/83 |
| 3,334,624 | 8/1967 | Schneider et al. | 128/92 |
| 3,626,935 | 12/1971 | Pollock et al. | |
| 3,759,257 | 9/1973 | Fischer et al. | 606/63 |
| 4,399,813 | 8/1983 | Barber | |
| 4,423,721 | 1/1984 | Otte et al. | |
| 4,450,834 | 5/1984 | Fischer | 606/104 |
| 4,531,517 | 7/1985 | Forte et al. | |
| 4,612,922 | 9/1986 | Barber | |
| 4,919,673 | 4/1990 | Willert et al. | 606/62 |
| 4,944,742 | 7/1990 | Clemow et al. | 606/59 |
| 4,981,481 | 1/1991 | Kranz et al. | |
| 5,013,314 | 5/1991 | Firica et al. | |
| 5,116,335 | 5/1992 | Hannon et al. | |
| 5,122,146 | 6/1992 | Chapman et al. | |
| 5,209,741 | 5/1993 | Spaeth | 604/164 |
| 5,321,391 | 6/1994 | Wilk | 604/264 |
| 5,395,317 | 3/1995 | Kambin | 604/170 |

OTHER PUBLICATIONS

George R. Dawson, Jr., "A Handy Pin Inserter," The Journal of Bone and Joint Surgery, 1947, p. 526.

Franklin et al., "Broken Intramedullary Nails", *J. Bone and Joint Surg.* 70A:1463-1471 (Dec., 1988).

Zimmer brochure, "ZMS Intramedullary Fixation Surgical Technique", Lit. No. 92-2236-02 (1990).

Brewster et al., "Extraction of Broken Intramedullary Nails—an Improvement in Technique", *Injury* 26:286 (1995).

Kyle and Winquist, "Surgical Techniques for Intramedullary Nail Extraction," in Zimmer Literature No. 97-0409-02, Intramedullary Nail Extraction Surgical Technique, (1995).

*Primary Examiner*—Michael Buiz
*Assistant Examiner*—Julian W. Woo
*Attorney, Agent, or Firm*—Townsend and Townsend and Crew

[57] ABSTRACT

A kit and method for retrieving a broken intramedullary nail from a medullary canal uses a first wire with a shaped tip and one or more second wires with substantially smooth tips. The first and second wires are extended through the broken nail. The wires are then wedged against the mouth of the intramedullary nail. A handle provided on the free end of the first wire is used to retrieve the intramedullary nail.

30 Claims, 3 Drawing Sheets

FIG. 1
FIG. 2A
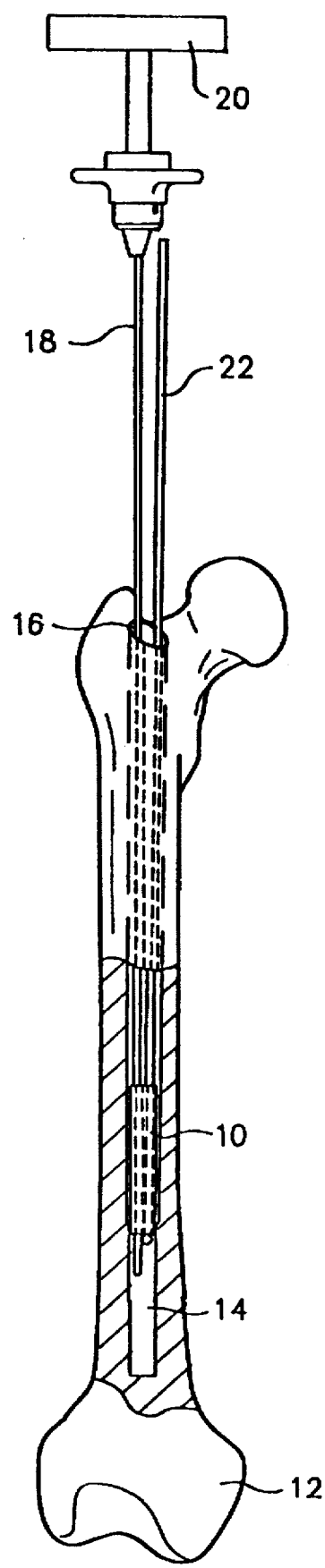
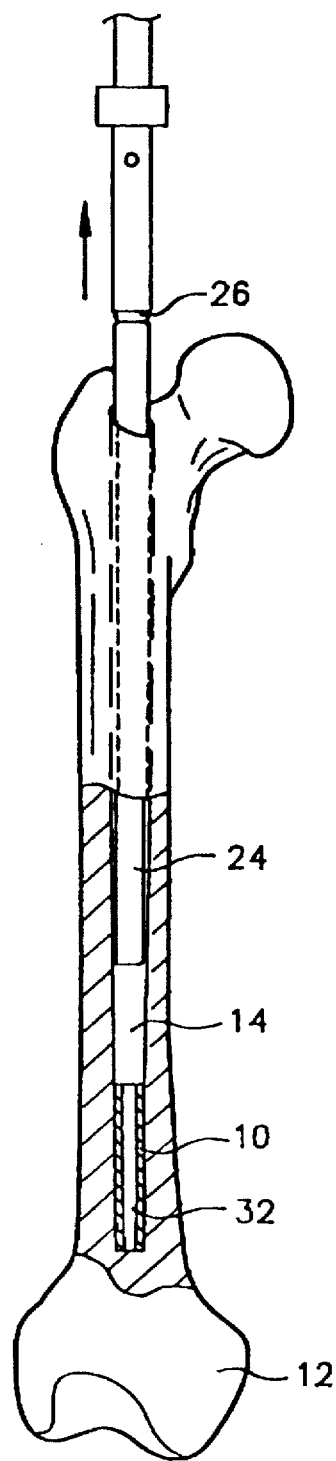

NAIL EXTRACTION KIT AND METHOD

BACKGROUND OF THE INVENTION

The present invention generally relates to the extraction of intramedullary nails. Particularly, the present invention relates to a kit and method for removing portions of broken intramedullary nails.

The use of inserts, such as intramedullary nails or rods, to repair fractures is known in the art. A variety of nail types and installation configurations exist. The availability and proven utility of these devices has led to their widespread use.

There are occasions when it becomes necessary to remove a broken intramedullary nail. Often the fracture has not yet properly healed or the bone has refractured. To properly reset the fracture the broken pieces of the nail must be removed from the canal so that a new insert can be installed. Even where a new insertion is not required, the broken nail may still require removal as it could cause discomfort due to movement of the pieces relative to each other.

In some situations, such as where the nail has not completely fractured, the entire nail may be removed using the kit designed for removal of the nail. One such removal kit is shown in U.S. Pat. No. 4,531,517, issued Jul. 30, 1985 to Forte et al. There, an extractor for nails is shown which employs an element designed to connect to a hook or ring at the proximal end of an inserted nail. Thus, the described extractor is limited in use; it can only remove full nails or the proximal end of nails having the proper hook or ring attachment.

Another removal kit is shown in U.S. Pat. No. 5,116,335, issued May 26, 1992 to Hannon et al, where a specific nail design may be extracted using a threaded rod and a power drill. The extraction kit, again, may only be used for that specially designed nail and only for the removal of a full nail or the proximal end of a broken nail. Thus, these extraction kits fail to address the problem of removal of a distal end of a broken intramedullary nail. Further, they can only extract compatible nail designs.

Some attempts have, however, been made to provide a device for the removal of remote pieces of broken nails. For example, U.S. Pat. No. 3,626,935, issued Dec. 14, 1971 to Pollock, et al., describes a surgical nail extractor which is designed to retrieve broken portions of nails having a cruciform cross section. The device uses sharp edged biting members which are rotated to bite into portions of the cruciform. Once a secure coupling is made between the nail and the biting members, the nail is extracted using a driver. Although this device is designed to retrieve remote pieces of broken nails, it suffers in that it is designed for nails having a special cross section. Not all nails are cruciform in cross section. Many have cylindrical, oval or other cross sectional shapes.

Standard tools have also been used to remove distal fragments of intramedullary nails. If the fragment is loose or small in diameter it may be possible to remove it with a grasping device such as a biopsy forceps, pituitary rongeur, or basket forceps. The procedure, however, is complicated if the distal fragment is tight or large in diameter. If the fragment is not solid or is not lodged too tightly, a osteotome can be inserted percutaneously to push the nail fragment proximally. This method requires that the bone be subject to one or more lateral stab wounds, impacting blood supply to the fracture and further damaging soft tissue.

Extraction hooks have also been used to extract distal nail fragments. The end of the hook is passed down the center of the nail fragment until it engages the distal edge of the fragment. The extraction hook is then retracted to retrieve the fragment. Unfortunately, the uneven force placed on the fragment often causes the nail to toggle in the canal, thereby lodging deeper into the canal wall. An unsuccessful removal can lodge the remote nail portion irretrievably within the canal, thus preventing further stabilization of the fracture using a replacement nail.

Accordingly, an intramedullary nail removal kit and method are needed which permit removal of remote broken pieces of nail. Advantageously, the kit and method should permit removal of a wide variety of nail types and cross sections without lodging the nail further or causing damage to the bone structure. The present invention fulfills these and other related needs.

SUMMARY OF THE INVENTION

According to the invention, a kit and method for retrieving a distal portion of a broken intramedullary nail from a medullary canal includes a first wire with a shaped tip and a second wire with a substantially smooth tip. The first and second wires are extended through the broken nail. The first wire is then retracted slightly to wedge the first and second wires against the remote mouth of the distal portion of nail. A handle provided on the free end of the first wire is used to pull the wire to retrieve the broken portion of intramedullary nail.

The kit and method of the present invention allow extraction of broken pieces of cannulated intramedullary nails of all shapes and cross sections without wedging the piece into walls of the canal and without the need to create further incisions into the bone.

Extraction of a distal portion of a broken nail may also involve first removing a proximal portion of that nail. This may be accomplished, e.g., through use of the standard tool designed for removal of a particular nail. Once the proximal portion is removed, a tool may be used to ream a portion of the exposed medullary canal to a size larger than the exterior diameter of the distal portion of broken nail. A flared exchange tube may then be inserted to guide the insertion of the first and second wires. The flared exchange tube is removed before extraction of the distal nail portion.

The removal kit of the present invention permits removal of both proximal and distal portions of a broken intramedullary nail through a single opening of the bone. No further entrances to the bone medulla are needed to extract all pieces of the nail, thereby minimizing soft tissue damage and preserving constant blood supply overlying the fracture.

For a fuller understanding of the nature and advantages of the invention, reference should be made to the ensuing description taken in conjunction with the accompanying drawings.

BRIEF DESCRIPTION OF THE DRAWINGS

FIG. 1 is a front cross-sectional view of a preferred embodiment of the extraction device of the present invention installed within a long bone; and FIGS. 2A–2E are front cross-sectional views depicting the use of an extraction device according to the present invention to extract a proximal portion of a broken intramedullary nail from a long bone.

DESCRIPTION OF THE SPECIFIC EMBODIMENTS

Figure 2B:
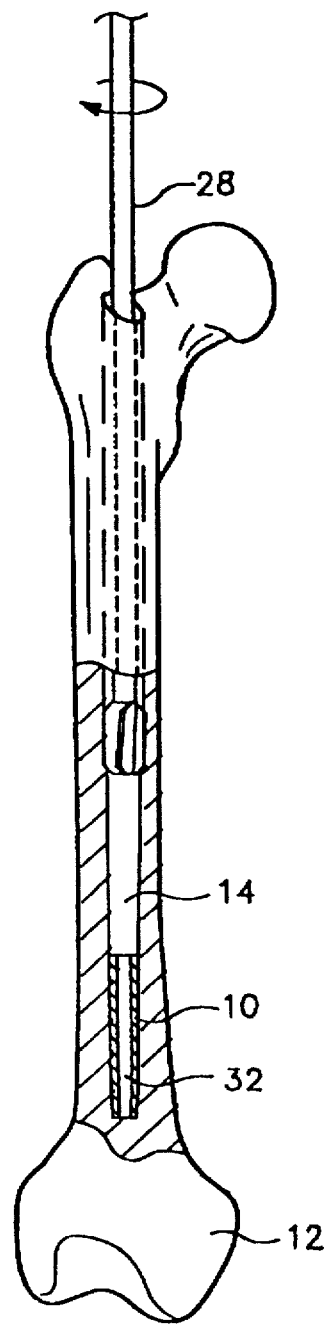

Details of the nail extraction method and apparatus according to the present invention will now be described.

Referring to FIG. 1, an embodiment of a kit according to the present invention is shown during removal of a distal nail portion 10 of an intramedullary nail. Often, the fracture for which the nail was inserted will require realignment. The bone 12 should, thus, be realigned during this procedure to ensure that the broken piece of nail is not impeded at the fracture site during extraction.

The distal nail portion 10 is shown lodged in a medullary canal 14 of a long bone 12, e.g., a femur. Those skilled in the art will recognize that the method and apparatus of the present invention can be used for the extraction of broken nails or pins from any of a number of bones, e.g., femur, tibia, humerus, fibula, ulna or radius. The proximal portion 24 of the nail is removed before the distal nail portion 10 is removed. The canal 14 is typically reamed to a size slightly greater than the diameter of the distal nail portion 10. A shaped-tip wire or rod 18 and a straight wire or rod 22 are inserted through the distal nail portion 10. As the shaped-tip wire 18 and the straight wire 22 are retracted, they wedge within or on the distal nail portion 10. The wires 18 and 22 may wedge within the cannulation of the distal portion, or may wedge in the mouth or opening of the cannulation with the enlarged portion catching against the edge of the distal tip of portion 10. The distal nail portion 10 may then be removed by applying force to the shaped-tip wire 18. A handle 20 may be used to facilitate removal of the distal nail portion 10.

Figure 2C:
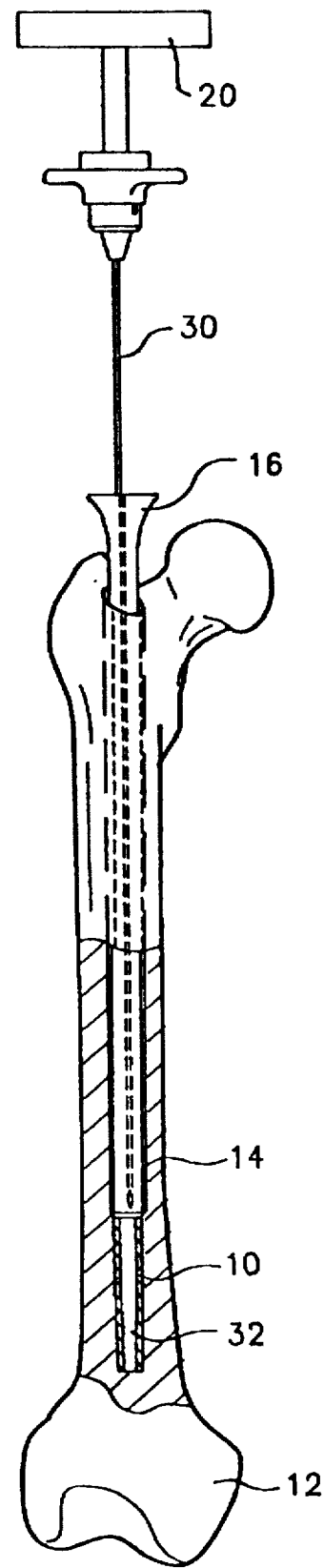
Figure 2D:
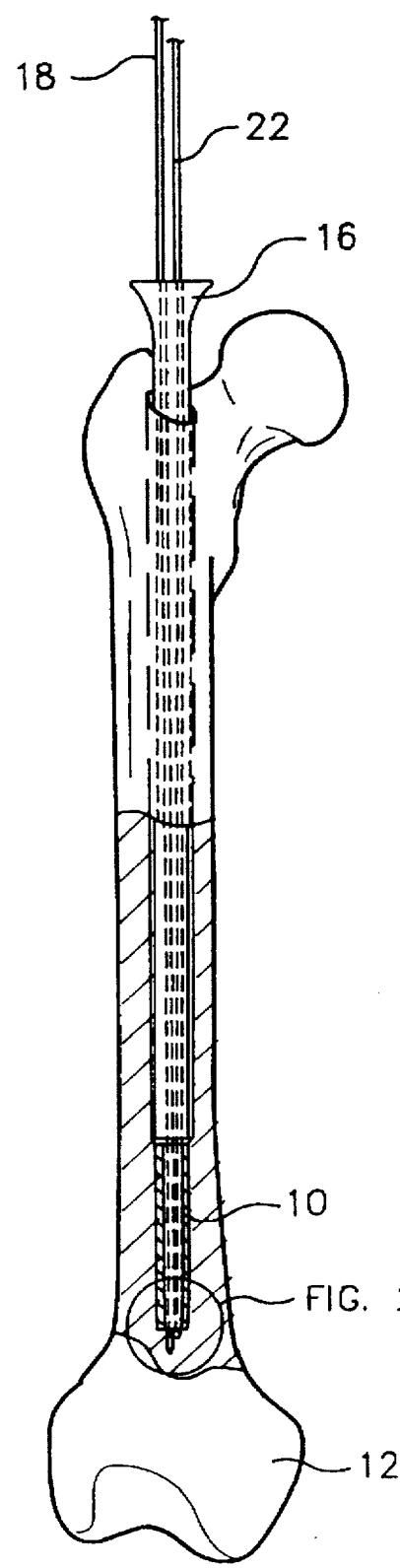
Figure 2E:
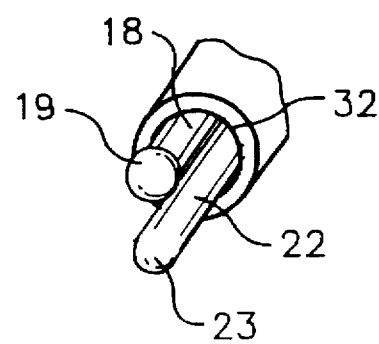

Details of use of the method and apparatus of the present invention will now be provided, referring to FIGS. 2A–2E which illustrate different stages of use of the apparatus. The proximal portion 24 of the nail, an elongated device having an internal hollow lumen or cannulation 32, as shown in FIG. 2E, must first be extracted. The nail is accessed through percutaneous incisions at the head of the nail. This reveals the interlocking screws (not shown) of the intramedullary nail, which may be utilized with an intramedullary nail and which can be removed using techniques well known in the art. As shown in FIG. 2A, the proximal portion 24 is readily extracted using the appropriate manufacturer's extraction device 26 for that particular intramedullary nail. Here, it is shown that the proximal portion 24 of the nail is longer than the distal nail portion 10. These nails, however, can fracture into any size pieces. Further, although rarer, they can fracture into more than two pieces requiring extraction of more than one remote piece. Thus, the relative proportions are intended to merely illustrate one particular removal scenario. Upon reading the disclosure, those skilled in the art will recognize that the method and kit of the present invention are capable of extracting any size or number of nail portion(s).

As shown in FIG. 2B, after the proximal nail portion 24 is removed from the medullary canal 14, the canal is typically reamed to be at least one size greater than the size of the broken nail, e.g. about 1 mm larger than the diameter of the nail. The medullary canal 14 may be reamed using any commonly available reaming device 28. The canal 14 should be reamed up to the distal portion 10 of the nail.

A flared exchange tube 16 may then be inserted into the expanded canal 14 (FIG. 2C). It is noted that the exchange tube would only be necessary if a non-healed or fresh fracture exists in the bone which could prevent the wires or pins from passing by the fracture. Otherwise, an exchange tube would not be needed. The flared exchange tube 16 is made, for example, of a disposable thin plastic and is sized to match the expanded diameter of the canal 14. The tube 16 is inserted until it abuts the distal nail portion 10. The flared exchange tube 16 will serve to guide the insertion of devices of the kit, and will be removed before extraction of the distal nail portion.

Some excess bone matter may exist in the canal 14 as a result of the removal of nail portion 24 and the reaming of the canal. This bone matter may be cleared using, e.g., a Steinmann pin 30 or any similar device designed to remove matter from small enclosed areas, as is known in the art. Any matter clogging the cannulation of the distal nail portion 10 should be removed. The size Steinmann pin 30 to be used may be determined by measuring the inner diameter of the proximal nail portion 24 which was previously removed. A pin 30 just smaller than the inner diameter should be chosen. The Steinmann pin 30 may be manipulated using a suitable gripping mechanism, such as an attachable T-shaped handle 20 to remove matter from the cannulation. The pin 30 should also be used to clear matter from the medullary canal beyond the distal nail portion 10. For example, an area of about 2–10 mm past the distal nail portion 10 should be clear of foreign matter. This will ensure proper insertion of the remaining tools of the extraction kit.

Referring now to FIG. 2D, the wires are now inserted into the bone 12. First, a wire 18 having its distal tip shaped to be larger than the diameter of the shaft of wire 18 is inserted through the exchange tube 16 and through the cannulation of the distal nail portion 10 so that it extends beyond the tip of portion 10. At least one straight wire 22 is then inserted through the exchange tube 16 and through the cannulation of the nail portion 10. Again, the tip 23 (shown in FIG. 2E) of the straight wire 22 should be inserted past the end of the nail portion 10. Preferably, the straight wire 22 extends further than the shaped-tip wire 18. For example, the tip 23 of straight wire 22 may extend about 6–10 mm past the end of the nail portion 10 when the shaped tip 19 extends 2–5 mm past the nail. The position of the shaped-tip wire 18 and the straight wire 22 may be verified by, e.g., image intensification or other means.

The straight wire 22 and the shaped-tip wire 18 are now manipulated to wedge the shaped tip 19 against the straight tip 23 in the opening of the distal nail portion 10. The size and shape of the shaped tip 19 should be selected to ensure a secure wedge against the straight tip 23 and the nail. The shaped end of wire 18 can be any of a wide variety of shapes so long as it is sufficient to be wedged against the distal end of the nail portion 10. For example, the shaped or expanded end of wire 18 can be elliptical, oval, oblong, bulb, round, diamond, square, triangle, hook (circumferential or straight), a right-angled protuberance from the wire 18, etc. The shaped end should be substantially nondeformable. The diameter of the enlarged shaped tip must be smaller than the diameter of the cannulation. The combined diameter of straight wire 22, plus the diameter of the enlarged portion of the shaped tip wire 18 should be larger than the diameter of the cannulation to provide a secure wedge. To achieve a secure wedge, it may be necessary to slightly push on the straight wire 22 while pulling on the shaped-tip wire 18. As shown in FIG. 2E, an advantage of enlarged shaped tip 19 is that no matter which way the shaft of wire 18 is rotated, it still provides the desired wedging with the distal portion 10 when wedged with secondary wire 22. The secure wedge which is formed ensures that the force used in removing the nail is directed along the center axis of the nail, allowing the nail to be evenly extracted without the toggling effect which may occur when an extraction hook is used by itself.

The flared exchange tube 16 may now be removed to permit extraction of the nail. A suitable wire gripping mechanism such as a wire grip T-handle 20 can be affixed to the top portion of the shaped-tip wire 18. This provides a secure grip to pull the wire 18. The distal nail portion 10 is thus securely wedged to the wires 18 and 22 and can be removed from the medullary canal 14, as shown in FIG. 1.

As will be appreciated by those familiar with the art, the present invention may be embodied in other specific forms without departing from the spirit or essential characteristics thereof. For example, although a bulb-shaped tip of a wire is preferred, other shaped tips may also be used with equal results. As mentioned above, the tip can be of any shape which fits through the center of the broken intramedullary nail and which can be wedged between the end of the nail and a straight wire. Further, the straight wire may also include a shaped tip if it still achieves the wedge effect.

The shaped-tip wire 18 and straight wire 22 can be a variety of lengths and diameters, and be made from a variety of materials having sufficient tensile strength to withstand the force applied to extract the nail portion 10 from the medullary canal, e.g., stainless steel, chrome cobalt alloys, etc. For example, preferred embodiments of the shaped tip wire 18 are of chrome cobalt alloy and have the following dimensions: (1) 1.6 mm in diameter, a bulb tip of 2.8 mm diameter, and a length of 60 cm; (2) 2.4 mm in diameter, a bulb tip of 4.0 mm diameter, and a length of 60 cm; (3) 3.2 mm in diameter, a bulb tip of 5.0 mm diameter, and a length of 60 cm; and (4) 3.2 mm in diameter, a bulb tip of 6.0 mm diameter, and a length of 60 cm. Preferred exemplary embodiments of the straight wire 22 for use with the foregoing shaped tip wire 18 are also of chrome cobalt alloy, have a length of 60 cm, and have a diameter of 1.6 mm, 2.0 mm, 3.2 mm, or 4.0 in diameter, with the 4.0 mm wire preferably being stainless steel. For packaging in kits, the components will generally include at least one and often a plurality, e.g., four or more of different size shaped wire 18 and at least one and often a plurality, e.g., four or more of different size straight wire 22, and will optionally contain a guide tube, T-shaped handle for grasping the shaped wire 18 or straight wire 22 and other components that may be useful in extracting a broken portion of an intramedullary nail from a medullary canal.

Accordingly, the disclosure of the invention is intended to be illustrative, but not limiting, of the scope of the invention which is set forth in the following claims.

What is claimed is:

1. A method for retrieving a cannulated intramedullary nail from a bone canal, comprising the steps of:

extending a shaped tip of a first wire through said nail until said shaped tip is positioned beyond a distal end of said nail;

extending a tip of a straight tip second wire through said nail until said tip is positioned beyond said distal end of said nail;

wedging said shaped tip of said first wire against said tip of said second wire and said distal end of said nail; and extracting said nail by retracting said first wire.

2. The method of claim 1, wherein said shaped tip is a bulb, oval, elliptical, diamond, oblong, round, square, triangle, circumferential hook, or straight hook, or is an angled protuberance from said tip.

3. The method of claim 2, wherein said shaped tip is a bulb.

4. The method of claim 1, wherein said nail is an intramedullary nail broken into a proximal and a distal portion, the method further comprising the step of removing said proximal portion of said intramedullary nail prior to extending said first wire through said distal portion of said intramedullary nail.

5. The method of claim 1, further comprising the step of enlarging a portion of said canal to a diameter larger than an exterior diameter of said nail.

6. The method of claim 5, further comprising the step of inserting a guide tube into said canal until an end of said guide tube abuts a proximal end of said distal portion of said nail.

7. The method of claim 6, further comprising the step of inserting a pin through said guide tube and through said distal portion of said nail to clear said portion of nail of foreign matter before said first wire is extended therethrough.

8. The method of claim 1, further comprising the step of verifying the position of said first wire prior to extracting said distal portion of said nail.

9. The method of claim 1, wherein the bone canal is of the femur, tibia, or humerus.

10. A combination used for retrieving a broken portion of a cannulated intramedullary nail from a medullary canal, comprising:

in combination with at least a portion of an intramedullary nail having a central cannula;

a first wire having a shaped tip at a first end; and a second wire having a substantially straight tip, wherein said shaped tip of said first wire and said substantially straight tip of said second wire each have a cross-sectional width less than an inner diameter of a cannula of said intramedullary nail to allow separate insertion of said shaped tip and said substantially straight tip through said cannula, and wherein said shaped tip and said substantially straight tip together have a combined cross-sectional width greater than said inner diameter of said cannula so that said shaped tip and said substantially straight tip form a cooperating wedge to forcibly engage a wall or distal opening of said cannula upon retraction of at least said first wire to facilitate removal of said broken portion of said nail.

11. The combination of claim 10, further comprising a handle for coupling to a second end of said first wire, whereby said first wire is pulled by said handle to retrieve said broken portion of said nail from the medullary canal.

12. The extraction kit of claim 10, further comprising a flared exchange tube for inserting in said medullary canal to accommodate passage of said first and second wires.

13. The extraction kit of claim 10, comprising a cleaning pin for insertion through said medullary canal and a center portion of said nail to remove foreign matter therefrom.

14. The combination of claim 10, comprising at least two first wires having a shaped tip at a first end of different sizes.

15. The extraction kit of claim 10, comprising at least two second wires having a substantially straight tip at a first end.

16. A combination 2 used for retrieving a broken portion of an intramedullary nail 3 from a medullary canal, comprising:

a first wire having a shaped tip at a first end; and at least two second wires of different diameter each having a substantially straight tip at a first end, wherein said shaped tip of said first wire and said substantially straight tip of at least one of said second wires are capable of being wedged in said broken portion of said nail.

17. The extraction kit of claim 10, wherein the tip of the first wire is shaped as a bulb, oval, elliptical, diamond, oblong, round, square, triangle, circumferential hook, or straight hook, or is an angled protuberance from said tip.

18. The extraction kit of claim 16, wherein the tip of the first wire is bulb shaped.

19. The combination of claim 16, further comprising a handle for coupling to a second end of said first wire, whereby said first wire is pulled by said handle to retrieve said broken portion of said nail from the medullary canal.

20. The combination of claim 16, further comprising a flared exchange tube for inserting in said medullary canal to accommodate passage of said first and second wires.

21. The combination of claim 16, further comprising a cleaning pin for insertion through said medullary canal and a center portion of said nail to remove foreign matter therefrom.

22. The combination of claim 16, including at least two first wires having a shaped tip at a first end of different sizes.

23. The combination of claim 16, wherein the tip of the first wire is shaped as a bulb, oval, elliptical, diamond, oblong, round, square, triangle, circumferential hook, or straight hook, or is an angled protuberance from said tip.

24. A kit used for retrieving a broken portion of a cannulated intramedullary nail from a medullary canal, comprising:

in combination with at least a portion of an intramedullary nail having a central cannula;

a first wire having a shaped tip at a first end; and a second wire having a substantially straight tip.

25. The combination of claim 24, wherein said shaped tip of said first wire and said substantially straight tip of said second wire each have a cross-sectional width less than an inner diameter of said cannula to allow separate insertion of said shaped tip and said substantially straight tip through said cannula, and wherein said shaped tip and said substantially straight tip together have a combined cross-sectional width greater than said inner diameter of said cannula so that said shaped tip and said substantially straight tip form a cooperating wedge to forcibly engage a wall or distal opening of said cannula upon retraction of at least said first wire to facilitate removal of said at least a portion of said nail.

26. The combination of claim 24, further comprising a handle for coupling to a second end of said first wire, whereby said first wire is pulled by said handle to retrieve said broken portion of said nail from the medullary canal.

27. The combination of claim 24, further comprising a flared exchange tube for inserting in said medullary canal to accommodate passage of said first and second wires.

28. The combination of claim 24, further comprising a cleaning pin for insertion through said medullary canal and a center portion of said nail to remove foreign matter therefrom.

29. The combination of claim 24, including at least two first wires having a shaped tip at a first end of different sizes.

30. The combination of claim 24, wherein the tip of the first wire is shaped as a bulb, oval, elliptical, diamond, oblong, round, square, triangle, circumferential hook, or straight hook, or is an angled protuberance from said tip.

* * * * *